US012622639B2

(12) United States Patent
Kuwabara et al.

(10) Patent No.: US 12,622,639 B2
(45) Date of Patent: May 12, 2026

(54) MEASUREMENT SYSTEM, MEASUREMENT METHOD, MEASUREMENT DEVICE, AND PROGRAM

(71) Applicant: NTT, Inc., Tokyo (JP)

(72) Inventors: Kei Kuwabara, Tokyo (JP); Kenichi Matsunaga, Tokyo (JP); Takayuki Ogasawara, Tokyo (JP)

(73) Assignee: NTT, INC., Tokyo (JP)

( * ) Notice: Subject to any disclaimer, the term of this patent is extended or adjusted under 35 U.S.C. 154(b) by 418 days.

(21) Appl. No.: 18/256,400

(22) PCT Filed: Dec. 8, 2020

(86) PCT No.: PCT/JP2020/045633
§ 371 (c)(1),
(2) Date: Jun. 7, 2023

(87) PCT Pub. No.: WO2022/123651
PCT Pub. Date: Jun. 16, 2022

(65) Prior Publication Data
US 2024/0016451 A1     Jan. 18, 2024

(51) Int. Cl.
*A61B 5/00*      (2006.01)
*A61B 5/301*     (2021.01)
*A61B 5/346*     (2021.01)

(52) U.S. Cl.
CPC .......... *A61B 5/6802* (2013.01); *A61B 5/0022* (2013.01); *A61B 5/301* (2021.01); *A61B 5/346* (2021.01); *A61B 2560/0242* (2013.01)

(58) Field of Classification Search
CPC ..... A61B 5/6802; A61B 5/0022; A61B 5/301; A61B 5/346; A61B 5/002; A61B 5/30;
(Continued)

(56) References Cited

U.S. PATENT DOCUMENTS

| | | | | |
|---|---|---|---|---|
| 2014/0119080 A1* | 5/2014 | Sakamoto | ............. | H02M 7/493 |
| | | | | 363/95 |
| 2015/0333671 A1* | 11/2015 | Sakai | ........................ | H04L 1/00 |
| | | | | 318/400.13 |
| 2017/0224244 A1 | 8/2017 | Kuwabara et al. | | |

FOREIGN PATENT DOCUMENTS

| | | | | | |
|---|---|---|---|---|---|
| CN | 110337679 B | * | 12/2021 | ............ | H04W 56/00 |
| WO | 2016024495 A1 | | 2/2016 | | |

OTHER PUBLICATIONS

CN 110337679 Translation (Year: 2021).*

* cited by examiner

*Primary Examiner* — Manuel L Barbee
(74) *Attorney, Agent, or Firm* — Slater Matsil, LLP

(57)     ABSTRACT

A measurement system includes a measurement unit configured to perform measurement a plurality of times on the basis of a first clock signal having a first clock period to obtain a plurality of measurement results, a time stamp provision unit configured to provide a time stamp indicating a measurement time to each measurement result obtained in the second period among the plurality of measurement results obtained using the measurement unit the basis of a second clock signal having a second clock period longer than the first clock period and having better period accuracy than the first clock signal, and a measurement time correction unit configured to correct a measurement time of a measurement result in accordance with a period specified using two time stamps and the number of measurement results obtained during the period.

11 Claims, 12 Drawing Sheets

(58) Field of Classification Search
CPC ... A61B 5/335; A61B 5/02438; A61B 5/0245;
A61B 5/112; A61B 5/332; A61B
2560/0242; A61B 2560/0209; H04Q 9/04
See application file for complete search history.

Fig. 12

| MEASUREMENT RESULT | MEASUREMENT TIME |
|---|---|
| HEART RATE: ···, RRI: ···, NUMBER OF STEPS: ···, POSTURE: ···, AIR TEMPERATURE: ··· | NOVEMBER 13, 2020 16:45:30 |
| HEART RATE: ···, RRI: ···, NUMBER OF STEPS: ···, POSTURE: ···, AIR TEMPERATURE: ··· | NOVEMBER 13, 2020 16:45:31 |
| HEART RATE: ···, RRI: ···, NUMBER OF STEPS: ···, POSTURE: ···, AIR TEMPERATURE: ··· | NOVEMBER 13, 2020 16:45:32 |
| · · · | |
| HEART RATE: ···, RRI: ···, NUMBER OF STEPS: ···, POSTURE: ···, AIR TEMPERATURE: ··· | NOVEMBER 13, 2020 17:45:29 |

MEASUREMENT SYSTEM, MEASUREMENT METHOD, MEASUREMENT DEVICE, AND PROGRAM

CROSS-REFERENCE TO RELATED APPLICATIONS

This application is a national phase entry of PCT Application No. PCT/JP2020/045633 filed on Dec. 8, 2020, which application is hereby incorporated herein by reference.

TECHNICAL FIELD

Embodiments of the present invention relates to a measurement system, a measurement method, a measurement device, and a program for obtaining a measurement result together with a measurement time.

BACKGROUND

In recent years, services have been used in which a small wearable sensor is used for continuously measuring a user's biological information or environmental information for a long period of time and the measurement results obtained through the measurement are used for health management and the like. As a technique used for such services, PLT 1 discloses a technique of measuring a heart rate and the like from an electrocardiographic potential which is an action potential of the heart using a wearable device and transmitting the measurement results obtained through the measurement to a smartphone or the like in real time or recording the measurement results in a memory.

CITATION LIST

Patent Literature

[PTL 1] PCT International Publication No. 2016/24495

SUMMARY

Technical Problem

Wearable sensors which are worn on a daily basis are required to be small and light, which limits battery capacity. Therefore, measurement with low power consumption is required for performing the measurement over a long period of time. Incidentally, there is a case in which it is desired to link and manage the measurement result and the user's activity at that time, and then analyze the measurement result while considering the user's activity. In this case, the correspondence relation between each of the measurement results and the user's activity is managed by the time. For this management, it is desirable that the measurement result is managed together with an accurate measurement time. Here, the measurement timing is generally controlled using a clock signal. If a highly accurate clock signal is used for measurement to accurately manage the measurement time as described above, power consumption will increase. On the other hand, if an oscillation circuit operating with low power consumption is used, the precision of the clock signal is reduced, and thus the accuracy of the measurement time is also reduced. Thus, there is a trade-off relationship between the power consumption and the accuracy of the measurement time. Note that such a trade-off occurs not only in wearable sensors but also in general measurement.

An object of embodiments of the present invention is to obtain, with low power consumption, a measurement result to which a measurement time having a small time lag with respect to a real time is provided.

Solution to Problem

In order to solve the problems described above, a measurement system includes: a measurement unit configured to perform measurement a plurality of times on the basis of a first clock signal having a first clock period to obtain a plurality of measurement results; a time stamp provision unit configured to provide a time stamp indicating a measurement time to each of two or more of the plurality of measurement results obtained through the measurement unit, the two or more of the plurality of measurement results being a part of the plurality of measurement results, on the basis of a second clock signal having a second clock period longer than the first clock period and having better period accuracy than the first clock signal; and a measurement time correction unit configured to correct a measurement time of a measurement result other than the measurement results to which the time stamp has been provided among the measurement results obtained during a period in accordance with a period specified using two time stamps of the time stamps provided to each of the two or more of the plurality of measurement results, which is a part of the plurality of measurement results, and the number of measurement results obtained during the period among the plurality of measurement results.

A measurement method includes: a measurement step of performing measurement a plurality of times on the basis of a first clock signal having a first clock period to obtain a plurality of measurement results; a time stamping providing step of providing a time stamp indicating a measurement time to each of two or more of the plurality of measurement results obtained through the measurement step, the two or more of the plurality of measurement results being a part of the plurality of measurement results, on the basis of a second clock signal having a second clock period longer than the first clock period and having better period accuracy than the first clock signal; and a measurement time correction step of correcting a measurement time of a measurement result other than the measurement result to which the time stamp is provided among the measurement results obtained during the period in accordance with a period specified using two time stamps of the time stamps provided to each of the two or more of the plurality of measurement results, which is a part of the plurality of measurement results, and the number of measurement results obtained during the period among the plurality of measurement results.

A measurement device includes: a measurement unit configured to perform measurement a plurality of times on the basis of a first clock signal having a first clock period to obtain a plurality of measurement results; and a time stamp provision unit configured to provide a time stamp indicating a measurement time to each of two or more of the plurality of measurement results obtained through the measurement unit, the two or more of the plurality of measurement results being a part of the plurality of measurement results, on the basis of a second clock signal having a second clock period longer than the first clock period and having better period accuracy than the first clock signal, in which the time stamp is used for correcting a measurement time of a measurement result other than the measurement result to which the time stamp is provided among the measurement results obtained during the period specified using two time stamps among the time stamps provided to each of the two or more of the plurality of measurement results, which is a part of the plurality of measurement results.

A program causes: a computer which acquires a plurality of measurement results obtained by performing measurement a plurality of times on the basis of a first clock signal having a first clock period and a time stamp indicating a measurement time provided to each of two or more of the plurality of measurement results, the two or more of the plurality of measurement results being a part of the plurality of measurement results, on the basis of a second clock signal having a second clock period longer than the first clock period and having better period accuracy than the first clock signal to function as: a measurement time correction unit configured to correct a measurement time of a measurement result other than the measurement result to which the time stamp is provided among the measurement results obtained during the period in accordance with a period specified using two time stamps of the time stamps provided to each of the two or more of the plurality of measurement results, which is a part of the plurality of measurement results, and the number of measurement results obtained during the period among the plurality of measurement results.

Advantageous Effects Embodiments of the Invention

According to embodiments of the present invention, it is possible to obtain a measurement result to which a measurement time having a small time lag with respect to an actual time is provided with low power consumption.

BRIEF DESCRIPTION OF THE DRAWINGS

FIG. 12 is a diagram showing a data structure in which each measurement result in a measurement result sequence is associated with a measurement time.

DETAILED DESCRIPTION OF ILLUSTRATIVE EMBODIMENTS

A measurement system 10 and the like according to an embodiment of the present invention will be described below with reference to the drawings.

Configuration of Measurement System 10

Figure 1:
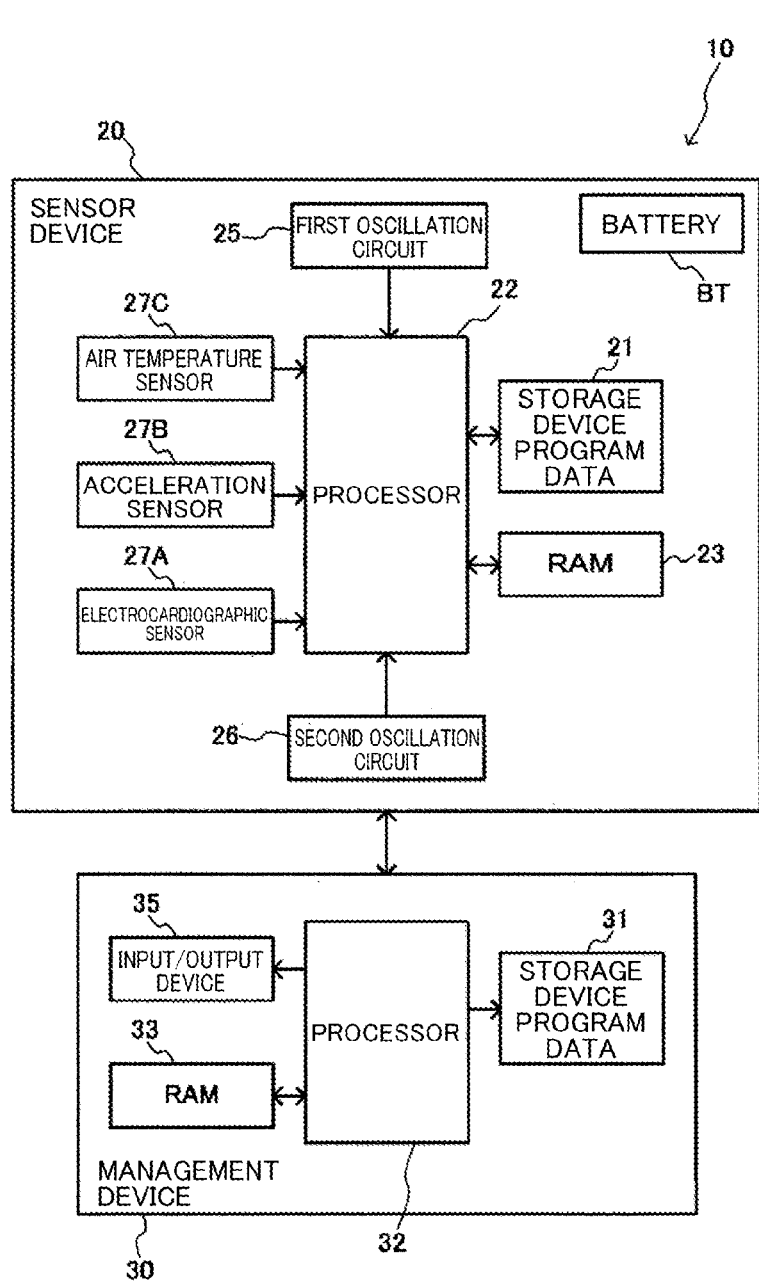
FIG. 1 is a hardware configuration diagram of a measurement system according to an embodiment of the present invention.
Figure 2:
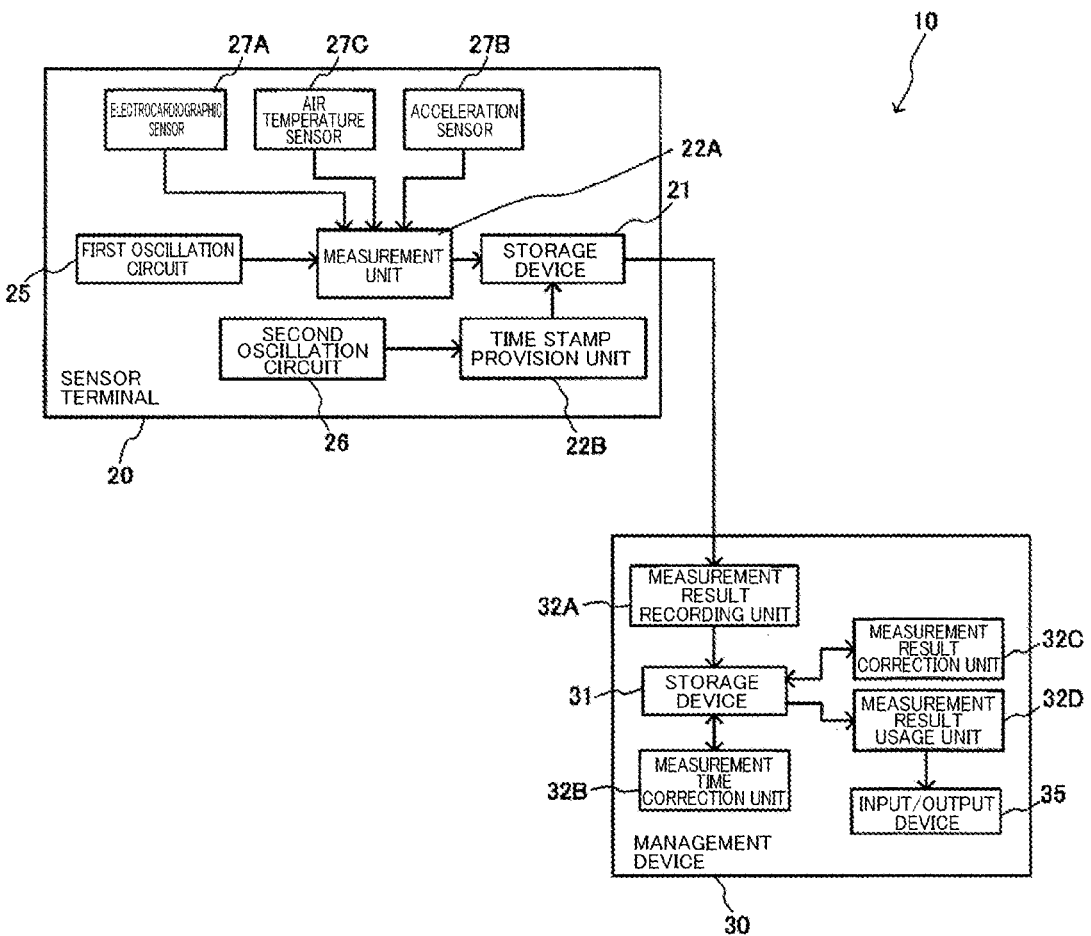
FIG. 2 is a block diagram showing a configuration of the measurement system according to the embodiment of the present invention.

The measurement system 10 shown in FIGS. 1 and 2 is possessed by a user, periodically measures the user's biological information and environmental information around the user a plurality of times, and manages each of measurement results which are each of measured biological information and environmental information, together with a measurement time. The biological information includes a heart rate, an R-R interval (RRI) which is an interval between two R waves in an electrocardiogram waveform, the number of steps, and a posture. The environment information includes an air temperature.

As shown in FIG. 1, the measurement system 10 includes a sensor device 20 and a management device 30. The sensor device 20 is composed of a wearable sensor attached to the clothes of the user and periodically measures the above biological information and environmental information. The management device 30 is composed of a computer such as a smartphone possessed by the user and stores and manages each measurement result obtained by the sensor device 20 periodically measuring.

The sensor device 20 includes a storage device 21, a processor 22, a random access memory (RAM) 23, a first oscillation circuit 25, a second oscillation circuit 26, an electrocardiographic sensor 27A, an acceleration sensor 27B, an air temperature sensor 27C, and a battery BT composed of batteries. Electric power required for an operation of the sensor device 20 is supplied from the battery BT.

The storage device 21 is a non-volatile storage device such as a hard disk, a flash memory, or a solid state drive (SSD) and stores programs and data. The processor 22 executes or uses programs and data stored in the storage device 21 to perform various processes such as measurement of the biological information and environment information (details will be described later). The processor 22 has a real-time clock (RTC) which holds a current time. The RAM 23 is a main memory of the processor 22.

The first oscillation circuit 25 oscillates a first clock signal having a first clock period and supplies it to the processor 22. The processor 22 measures the user's biological information and environment information on the basis of the first clock signal (refer to a measurement unit 22A which will be described later).

The second oscillation circuit 26 oscillates a second clock signal having a second clock period longer than the first clock period and a higher period precision than the first clock signal and supplies the second clock signal to the processor 22. The period accuracy can also be said to be the accuracy of the clock frequency accuracy. The RTC of the processor 22 updates the current time every second on the basis of the second clock signal. The RTC, for example, divides a frequency of the second clock signal and updates it every second. The processor 22 provides the current time updated using the RTC as a time stamp to the result of the measurement based on the first clock signal (refer to a time stamp provision unit 22B which will be described later). The time stamp indicates the measurement time of the provided measurement result.

The electrocardiographic sensor 27A, the acceleration sensor 27B, and the air temperature sensor 27C are used for measuring the biological information and the environment information. The electrocardiographic sensor 27A includes a bioelectrode which is in contact with the user's skin, detects an electrocardiographic potential of the user under the control of the processor 22 using bioelectrodes, and supplies the detected electrocardiographic potential to the processor 22. The processor 22 measures the heart rate and the RRI among the biological information on the basis of the electrocardiographic potential. The acceleration sensor 27B detects acceleration under the control of the processor 22 and supplies the detected acceleration to the processor 22. The processor 22 measures the number of steps and a posture of the biological information on the basis of the acceleration. The air temperature sensor 27C detects the air temperature included in the environment information under the control of the processor 22 and supplies the detected air temperature to the processor 22.

The management device 30 includes a storage device 31, a processor 32, a RAM 33, and an input/output device 35.

The storage device 31 is a non-volatile storage device such as a hard disk, a flash memory, or an SSD and stores programs and data. The processor 32 executes or uses programs and data stored in the storage device 31 to perform various processes such as management of the measurement results (details will be described later). The RAM 33 is a main memory of the processor 32. The input/output device 35 is composed of a touch panel or the like.

The sensor device 20 and the management device 30 each include a communication module (not shown) and are configured to be able to communicate with each other wirelessly or by wire.

As shown in FIG. 2, the sensor device 20 includes a measurement unit 22A and a time stamp provision unit 22B. Each of the units 22A and 22B is composed of a processor 22 (FIG. 1) which executes a program stored in the storage device 21.

A first clock signal is input from the first oscillation circuit 25 to the measurement unit 22A. The measurement unit 22A operates on the basis of the first clock signal and periodically measures biological information and environment information for a long period of time. For example, the measurement unit 22A counts a rising edge of a pulse of the first clock signal and operates every 1 millisecond by operating each time a count value reaches a predetermined value. The measurement unit 22A may divide a frequency of the first clock signal up to 1 kHz and operate every 1 millisecond on the basis of the divided clock signal. The first clock period of the first clock signal which realizes the operation every 1 ms (millisecond) is shorter than the second clock period (generally, 1/32768 seconds) of the second clock signal used for the RTC.

The measurement unit 22A periodically detects a cardiac potential using the electrocardiographic sensor 27A. Detection may be performed, for example, every arbitrary time within the range of 1 to 8 ms. Here, the measurement unit 22A performs the detection operation at one operation timing, that is, every 1 millisecond. The detected electrocardiographic potentials are stored in the RAM 23 (FIG. 1) for a certain period of past time from the most recent one and used for measuring an RRI and a heart rate. The measurement unit 22A detects R waves on the basis of a change in the electrocardiographic potential. The measurement unit 22A measures the RRI by specifying a time interval between two R waves. Here, each period such as a time interval is specified using the number of electrocardiographic potentials detected within that period×the detection cycle (here, 1 ms) in which the measurement unit 22A detects the electrocardiographic potential. The RRI is specified using the number of new potentials detected×the period of detection between two R waves. The detection period is a period based on the first clock period when it is assumed that there is no error in the first clock period. The number of RRIs included in one second varies depending on the heart rate and the range from 0 to 5. The measurement unit 22A measures the heart rate by counting the number of R waves per 60,000 electrocardiographic potentials, that is, per 60 seconds. In this manner, the measurement unit 22A measures a heart rate and an RRI on the basis of the first clock signal.

The measurement unit 22A periodically detects acceleration using the acceleration sensor 27B. A sampling frequency for specifying the number of steps and a posture may be about 20 Hz. Therefore, the measurement unit 22A detects the acceleration every time the operation timing every 1 ms arrives 5 times, that is, every 5 milliseconds. This reduces power consumption and a data volume. The detected accelerations for a certain period from the latest to the past are stored in the RAM 23 and used for measuring the number of steps and a posture. The measurement unit 22A measures the number of steps and a posture on the basis of a change in acceleration. The number of steps is the number of walking steps. Posture measurement is performed by referring to a table prerecorded in the storage device 21, for example, to classify an acceleration change mode into one of posture classification codes from 00 to 04. Here, for example, 00 indicates a supine position, 01 indicates a sitting position, 02 indicates a standing position, 03 indicates walking, and 04 indicates running.

The measurement unit 22A periodically measures a temperature using the air temperature sensor 27C. Since the temperature does not change abruptly, the measurement interval may be, for example, every 1000 operation timings of 1 ms, that is, every 1 second. This reduces power consumption and a data amount for measurement.

It is preferable that the measurement unit 22A detect the cardiac potential at intervals of 1 ms on the basis of the first clock signal, detect the acceleration every 5 times the cardiac potential is detected, and measure the temperature every 1000 times the cardiac potential is detected. Thus, since the first clock signal is shared by multiple types of detection and measurement, the measurement unit 22A can efficiently synchronize a plurality of types of detection and measurement.

Figure 3:
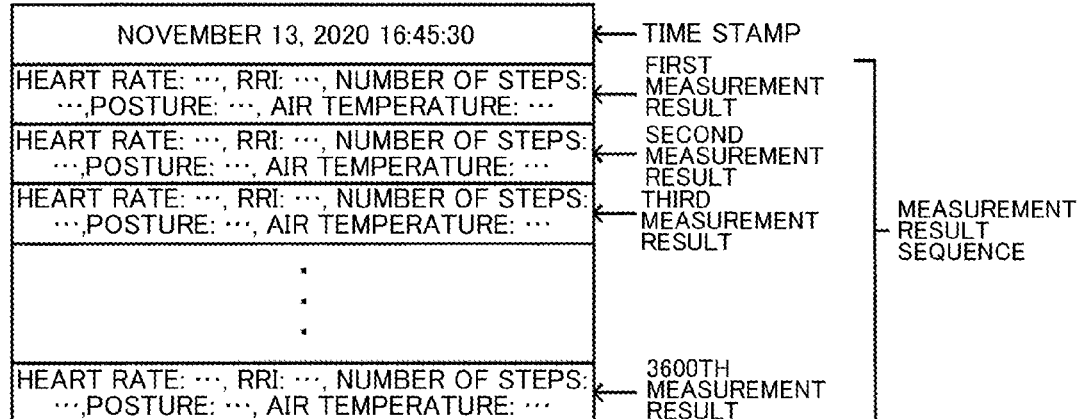
FIG. 3 is a diagram showing a configuration example of a measurement result sequence and time stamps.

The measurement unit 22A measures the heart rate, the RRI, the number of steps, the posture, and the temperature each time the 1 ms operation timing based on the first clock period reaches 1000 times, that is, every second. In this manner, the measurement unit 22A periodically performs measurement a plurality of times at the measurement cycle $T_{cycle}$ (1 second) on the basis of the first clock signal to obtain a plurality of measurement results. The measurement unit 22A records the measured heart rate, the RRI, the number of steps, the posture, and the temperature in the storage device 21 as one measurement result for each measurement. Thus, 3600 measurement results are recorded in the storage device 21 in one hour. The measurement results are recorded in chronological order. The measurement unit 22A counts the number of measurement results recorded in the storage device 21 using a counter provided in the RAM 23. The measurement unit 22A transmits the 3600 measurement results to the management device 30 as a measurement result sequence as shown in FIG. 3 every time the counter value reaches 3600 and 3600 measurement results are recorded in the storage device 21, that is, every hour. The measurement result sequence is deleted from the storage device 21 and the counter is reset using this transmission as a trigger. 24 measurement result sequences are generated in 24 hours.

As shown in FIG. 3, in the measurement result sequence, 3600 measurement results are arranged in order of measurement. A time stamp is provided to the measurement result sequence. The time stamp is provided by the time stamp provision unit 22B as will be described later and indicates the measurement time of the first measurement result in the measurement result sequence. The time stamp is transferred together with the measurement result sequence when the measurement result sequence is transferred.

The time stamp provision unit 22B shown in FIG. 2 includes the RTC of the processor 22 and provides the current time updated using the RTC to the measurement result sequence as a time stamp indicating the measurement time. The RTC updates the current time on the basis of the second clock signal. Therefore, the time stamp provision unit 22B provides time stamps to the measurement result sequence on the basis of the second clock signal.

The time stamp provision unit 22B operates on the basis of the first clock signal or the internal clock signal of the processor 22 and reads the current time from the RTC at a timing at which the first measurement result among the 3600 measurement results forming the measurement result sequence is obtained. For example, the current time is read each time the count value of the above-described counter that counts the number of measurement results recorded in the storage device 21 becomes 1. The time stamp provision unit 22B stores the read current time as a time stamp in the storage device 21 in association with the first measurement result, thereby providing this time stamp to the first measurement result. This time stamp indicates the measurement time of the first measurement result. When the second to 3600th measurement results are recorded in the storage device 21 after the time stamp is provided, the time stamp is provided to the entire measurement result sequence. It can be said that the time stamp indicates the measurement start time in the measurement result sequence.

The measurement time of each measurement result included in the measurement result sequence to which the time stamp is provided is specified using a measurement time $T_{timestamp}$ indicated by the time stamp, an order P of the measurement result in the measurement result sequence, and a measurement cycle $T_{cycle}$ based of one clock signal when there is no periodic error. For example, the measurement time Tm is obtained by $$Tm = T_{timestamp} + T_{cycle} \times (P-1) \tag{1}.$$

For example, the measurement time Tm of the third measurement result in the measurement result sequence of FIG. 3 is 16:45:30 on Nov. 13, 2020+1 second×(3-1)=16:45:32 on Nov. 13, 2020.

As described above, the measurement time of each measurement result included in the measurement result sequence is specified based on the time stamp and the measurement cycle $T_{cycle}$. Here, since the measurement cycle $T_{cycle}$ is a fixed value, the providing of the time stamp means that the measurement time is provided to not only the first measurement result but also the second and subsequent measurement results. The measurement cycle $T_{cycle}$ is based on the first clock period of the first clock signal and the periodic accuracy of the first clock period is lower than that of the second clock period. Therefore, a periodic error may occur in the first clock signal which causes an error in the measurement cycle $T_{cycle}$. As a result, errors may occur in the measurement times of the second and subsequent measurement results included in the measurement result sequence. Therefore, in the embodiment, the measurement time provided to each measurement result on the sensor device 20 side is corrected on the management device 30 side.

As shown in FIG. 2, the management device 30 includes a measurement result recording unit 32A, a measurement time correction unit 32B, a measurement result correction unit 32C, and a measurement result usage unit 32D. Each of the units 32A to 32D is composed of the processor 32 (FIG. 1) which executes programs stored in the storage device 31.

The measurement result recording unit 32A sequentially receives the measurement result sequence transmitted from the sensor device 20 every hour and the time stamp provided to the measurement result sequence and records them in the storage device 31 in chronological order.

The measurement time correction unit 32B corrects the measurement times of the measurement results other than the measurement results indicated by the time stamps provided to the measurement result sequence, that is, each of the second to 3600th measurement results other than the first measurement result associated with the time stamp, among the 3600 measurement results included in the measurement result sequence recorded in the storage device 31.

Figure 4:
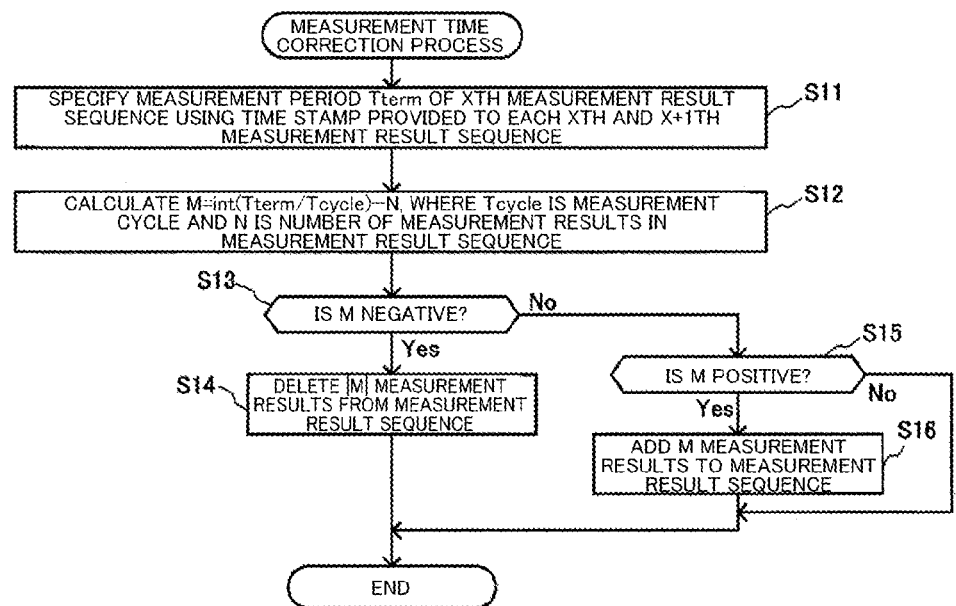
FIG. 4 is a flowchart for describing measurement time correction process performed using a measurement time correction unit in FIG. 2.

The measurement time correction unit 32B corrects the measurement time by, for example, performing the measurement time correction process shown in FIG. 4. The measurement time correction process is performed at an arbitrary timing after two or more measurement result sequences are recorded in the storage device 31. The measurement time correction process is performed on each measurement result sequence stored in the storage device 31. In the following description, the chronological order of the measurement result sequence to be processed is Xth.

In the measurement time correction process shown in FIG. 4, the measurement time correction unit 32B specifies the measurement period $T_{term}$ during which 3600 measurement results are obtained from 3600 measurements for obtaining the Xth measurement result sequence using the time stamps provided to the Xth and X+1th measurement result sequences (Step S11). As described above, each time stamp provided to the measurement result sequence indicates the measurement time of the first measurement result in the measurement result sequence. Therefore, in Step S11, the measurement period $T_{term}$ of the Xth measurement result sequence is specified by obtaining the difference period obtained by subtracting the measurement time indicated by the Xth time stamp from the measurement time indicated by the X+1th time stamp.

Subsequently, the measurement time correction unit 32B obtains a numerical value M by the following Expression (2) on the basis of the measurement cycle $T_{cycle}$=1 second based on the first clock signal when there is no periodic error, the number N of measurement results forming the measurement result sequence N=3600, and the measurement period $T_{term}$ specified in Step S11 (Step S12). Here, int(x) in the following Expression (2) is an integer conversion operation of x. Since x, that is, $T_{term}/T_{cycle}$, is a positive value, int(x) is a value obtained by truncating the decimal point of x.

$$M=\mathrm{int}(T_{term}/T_{cycle})-N \qquad (2)$$

The int($T_{term}/T_{cycle}$) specifies the number of measurements or the number of measurement results performed in the measurement cycle $T_{cycle}$ when there is no periodic error of the first clock signal in the measurement period $T_{term}$. If int($T_{term}/T_{cycle}$) is 3600, it means that there is no periodic error in the first clock signal and M is zero.

After Step S12, the measurement time correction unit 32B determines whether the value of M is negative (Step S13). When M is a negative value (Step S13; Yes), the number of measurement results actually obtained in the measurement period $T_{term}$ (=3600) is |M| more than the number of measurement results which need to be obtained in the measurement period $T_{term}$ assuming that there is no periodic error in the first clock signal. Therefore, the measurement cycle $T_{cycle}$ is shorter than 1 second when there is no periodic error. Therefore, when M is a negative value, the measurement time correction unit 32B performs processing for deleting |M| pieces of measurement results from the Xth measurement result sequence (Step S14). Thus, the measurement cycle $T_{cycle}$ is corrected to the original one second without a periodic error, and as a result, the measurement time of each measurement result in the Xth measurement result sequence is corrected to the measurement time calculated by the above Expression (1).

Figure 5:
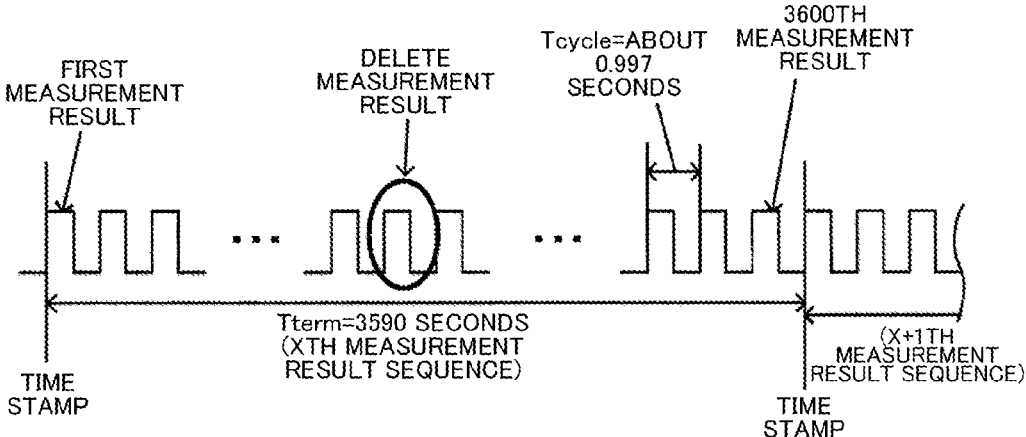
FIG. 5 is a schematic diagram for explaining a process of deleting a measurement result from a measurement result sequence in a measurement time correction process of FIG. 4 and is a schematic diagram before deleting the measurement result.
Figure 6:
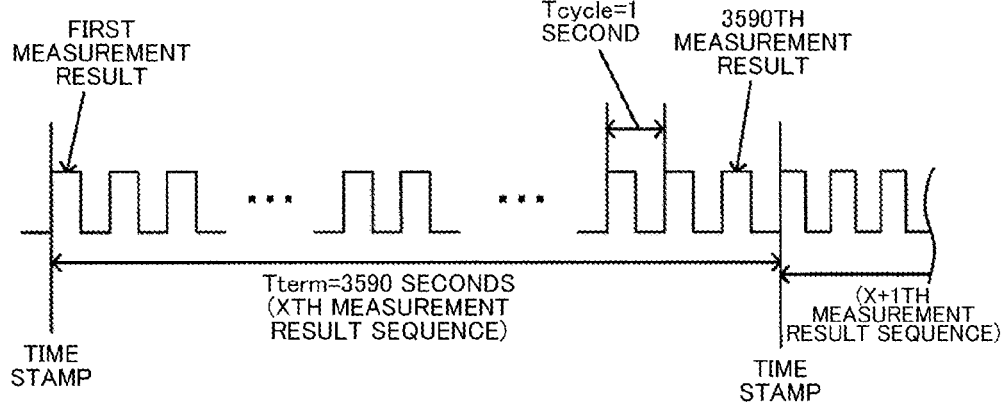
FIG. 6 is a schematic diagram for explaining the process of deleting a measurement result from a measurement result sequence in the measurement time correction process of FIG. 4 and is a schematic diagram after deleting the measurement result.

For example, assuming that the measurement period $T_{term}$ of the Xth measurement result sequence is 3590 seconds as shown in FIG. 5, M=−10. In this case, the measurement cycle $T_{cycle}$ including the periodic error is about 0.3% shorter than the original measurement cycle $T_{cycle}$ without the periodic error on the basis of the second clock signal with less periodic error than the first clock signal and is about 0.997 seconds. For this reason, the first clock period is also shortened accordingly. In this case, as shown in FIGS. 5 and 6, it is assumed that 3590 measurement results are obtained in the measurement period $T_{term}$ of 3590 seconds by deleting |M|=10 measurement results from the 3600 measurement results forming the measurement result sequence. Thus, the measurement cycle $T_{cycle}$ is corrected to the original one second.

When M is not a positive value (Step S13; No), the measurement time correction unit 32B determines whether M is a positive value (Step S15). The measurement time correction unit 32B ends the measurement time correction process without correction because there is no periodic error in the first clock signal when the value is not positive (Step S15; No). On the other hand, when M is a positive value (Step S15; Yes), the number of measurement results actually obtained in the measurement period $T_{term}$ (=3600) is M less than the number of measurement results which need to be obtained in the measurement period $T_{term}$ when the first clock signal does not have a periodic error. Thus, the measurement cycle $T_{cycle}$ is longer than 1 second when there is no periodic error. Therefore, when M is a positive value, the measurement time correction unit 32B adds M new measurement results to the Xth measurement result sequence (Step S16). Thus, the measurement cycle $T_{cycle}$ is corrected to the original one second, and as a result, the measurement time of each measurement result in the Xth measurement result sequence is corrected to the measurement time calculated by the above Expression 1.

Figure 7:
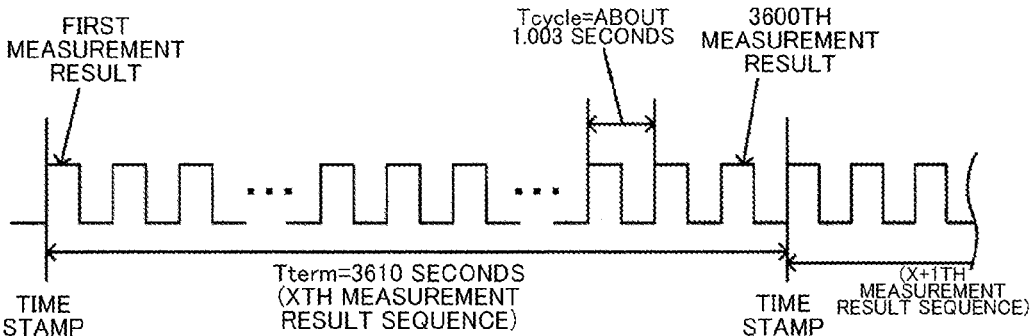
FIG. 7 is a schematic diagram for explaining a process of adding a measurement result to a measurement result sequence in the measurement time correction process of FIG. 4 and is a schematic diagram before adding the measurement result.
Figure 8:
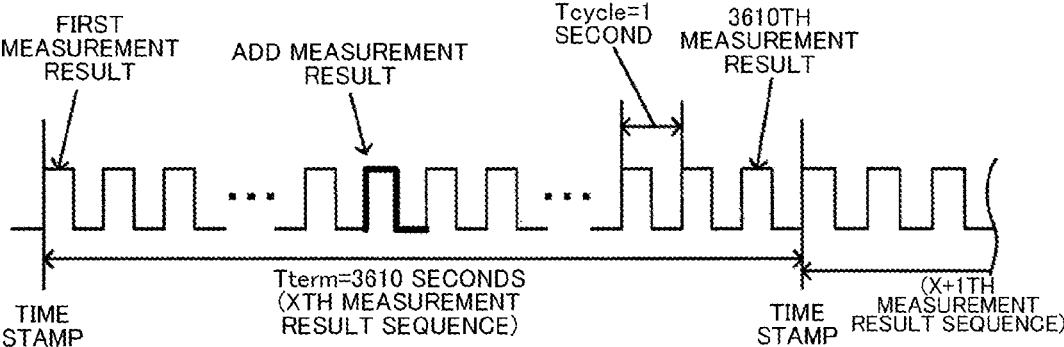
FIG. 8 is a schematic diagram for explaining the process of adding a measurement result to a measurement result sequence in the measurement time correction process of FIG. 4 and is a schematic diagram after adding the measurement result.

For example, assuming that the measurement period $T_{term}$ of the X-th measurement result sequence is 3610 seconds as shown in FIG. 7, M=10. In this case, the measurement cycle $T_{cycle}$ including the periodic error is about 1.003 seconds longer than the original measurement cycle $T_{cycle}$ without the periodic error by about 0.3% on the basis of the second clock signal which has less periodic error than the first clock signal and is about 1.003 seconds. Therefore, the first clock period is also longer by that amount. In this case, as shown in FIGS. 7 and 8, it is assumed that 3610 measurement results are obtained in the measurement period $T_{term}$ of 3610 seconds by adding M=10 new measurement results to the 3600 measurement results which constitute the measurement result sequence. Thus, the measurement cycle $T_{cycle}$ is corrected to the original one second.

The measurement time correction unit 32B may delete or add the measurement result so that the number of measurement results forming the Xth measurement result sequence is brought closer to the number of measurement results originally obtained in the measurement period $T_{term}$ (including matching) when there is no periodic error in the first clock signal and the method is arbitrary.

Although the position in which the measurement result is added to the measurement result sequence or the position of the measurement result to be deleted is arbitrary, it is preferable to distribute the respective positions within the measurement result sequence so that the details of the measurement result sequence does not change significantly before and after the addition or deletion of the measurement result. For example, the positions are arranged so that one or more measurement results are located between the positions. For example, the positions are evenly distributed within the measurement result sequence and the number of measurement results between insertion positions or the number of measurement results between deletion positions is the same. More specifically, a measurement result is added to or deleted from the measurement result sequence every N/(|M|+1) measurement results. Specifically, when increasing 3600 measurement results to 3610, N=3600, |M|=10, and N/(|M|+1)≈327 are satisfied and the measurement results are added after the 327th, 654th, 981st, 1308th, 1635th, 1962nd, 2289th, 2616th, 2943rd, and 3270th measurement results in the measurement result sequence. Also, when reducing the number of measurement data sets from 3600 to 3590, the process of deleting the measurement results in the above order may be performed in the same manner as described above.

When a new measurement result is added after the Hth measurement result in the measurement result sequence, the details of the measurement result to be added corresponds to the details of each of the Hth and H+1th measurement results before and after it. This point will be described below with reference to FIGS. 9 and 10.

Of the new measurement results to be added, an average value of the values of the previous and subsequent measurement results is adopted for values of the kind which are recorded periodically and change continuously, such as a heart rate and a temperature. As a modification example, the numerical value may be the same as the numerical value of the previous or subsequent measurement result sequence.

Figure 9:
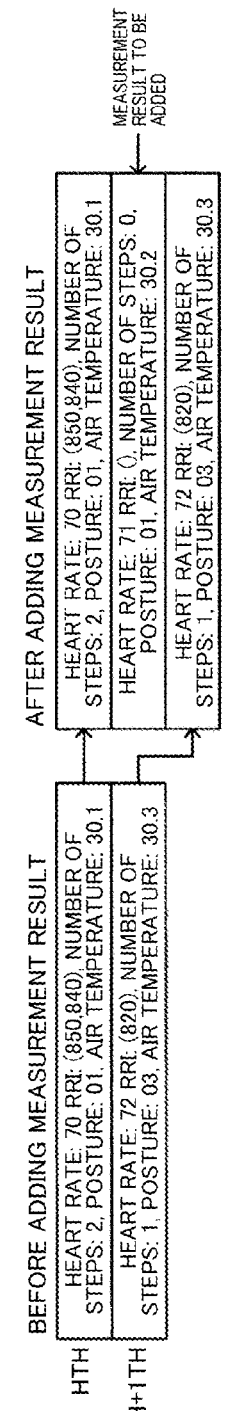
FIG. 9 is a diagram showing an example of processing for adding a measurement result to a measurement result sequence in the measurement time correction process of FIG. 4.
Figure 10:
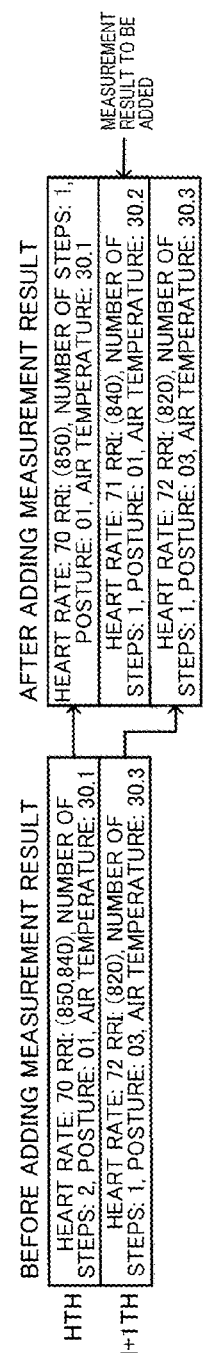
FIG. 10 is a diagram showing another example of the process of adding a measurement result to a measurement result sequence in the measurement time correction process of FIG. 4.

Of the new measurement results to be added, the same values as those of the previous or subsequent measurement results are adopted for numerical values which are recorded periodically and change discontinuously such as a posture. In FIGS. 9 and 10, the same values as the previous, that is, an Hth measurement result are used.

A state in which an event does not occur as shown in FIG. 9, for example, a state in which there is no RRI value, 0 steps, and the like is adopted for event-like numerical values that occur irregularly such as the RRI and the number of steps among the new measurement results to be added. Thus, for example, the total number of steps in the measurement result sequence can be matched before and after addition of the measurement result. Furthermore, as shown in FIG. 10, a part of the numerical value in the previous or subsequent measurement result (here, RRI of the previous Hth measurement result: 840, number of steps: 1) may transition to the measurement results to be added while maintaining each numerical value of the RRI or the total number of steps.

When deleting the Hth measurement result in the measurement result sequence, the details of the measurement result to be deleted may be sorted into the H−1th and H+1th measurement results before and after it. This point will be described below with reference to FIG. 11.

Of the measurement results to be deleted, values such as a heart rate and a temperature which are recorded periodically and change continuously and numerical values such as a posture which are recorded periodically and change discontinuously may simply be deleted.

Figure 11:
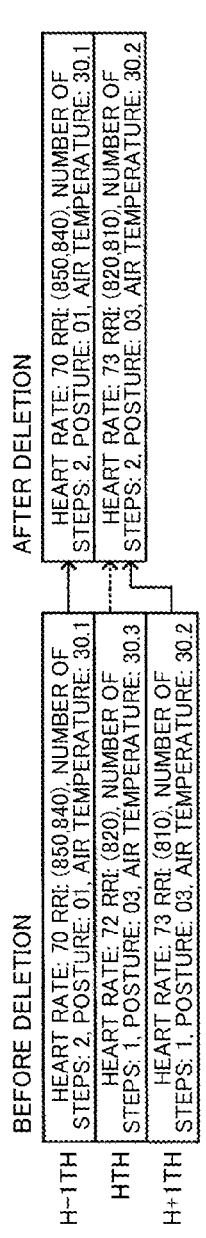
FIG. 11 is a diagram showing another example of processing for deleting a measurement result from a measurement result sequence in the measurement time correction process of FIG. 4.

Of the measurement results to be deleted, if event-like numerical values such as an RRI and the number of steps which occur irregularly are simply deleted, there will be an inconvenience in which the numerical value of an RRI and the total number of steps will not match before and after deletion. Therefore, such values transitions to previous or subsequent measurement results. In FIG. 11, the numerical values of RRI=820 ms and the number of steps=1 included in the Hth transition to the H+1 th measurement result. In this way, when deleting the measurement results, the measurement time correction unit 32B avoids the discrepancy by not deleting the predetermined specific type of measurement results but transiting to other measurement results. Particularly, the above-described discrepancies can be avoided with a small amount of processing by transitioning the result of a predetermined specific type of measurement to at least one of before and after the measurement result to be deleted.

As described above, when adding or deleting a measurement result to or from the measurement result sequence, the measurement time correction unit 32B adds or deletes the measurement result using only the details of the measurement result before, after, or both of the positions in which the measurement result is to be added or deleted. This makes it possible to correct the measurement time with a small amount of processing even for a large amount of measurement results recorded over a long period of time.

The measurement result correction unit 32C shown in FIG. 2 corrects the time interval such as the RRI measured on the basis of the first clock signal among the measurement results of the measurement result sequence stored in the storage device 31. When a periodic error occurs in the first clock period of the first clock signal, an error also occurs in the numerical value of the RRI. Thus, the measurement result correction unit 32C corrects the error using the time stamp.

Specifically, assuming that the measurement cycle based on the first clock signal when there is no periodic error is $T_{cycle}$, the measurement period, which is the difference between the two timestamps, is $T_{term}$, and the number of measurement results obtained during $T_{term}$ is N, the measurement result correction unit 32C corrects the RRI by multiplying the RRI by a correction coefficient C calculated by the following Expression 3.

$$C = T_{term} / (T_{cycle} \times N) \tag{3}$$

For example, assuming that the RRI measured on the basis of the first clock signal is 800 ms, N=3600, $T_{cycle}$=1 second, and $T_{term}$=3610 seconds, a correction coefficient C is approximately 1.003 and which is multiplied by the RRI of 800 msec to obtain a corrected RRI of 802 msec.

The measurement result usage unit 32D uses the measurement result sequence and the time stamp stored in the storage device 31 to perform various processes. For example, the measurement result usage unit 32D displays a graph or the like showing a relationship between the corrected measurement time and the measurement result in an input/output device 35. At this time, the measurement result usage unit 32D displays the activity details of a user separately input to the management device 30 together with the time in association with the measurement result (for example, heart rate) with the time as a common axis. Furthermore, the measurement result usage unit 32D analyzes the user's health and the like on the basis of the relationship between the user's activity details and the measurement result (for example, heart rate) using the time as common.

Effects and the Like of Embodiment

Since the sensor device 20 is a wearable sensor in the embodiment, the biological information and the environment information are measured continuously for a long period of time. In this case, the first oscillation circuit which oscillates the first clock signal needs to be operated all the time. On the other hand, since the battery BT of the sensor device 20 has a small size, the capacity thereof is also limited. Therefore, the first oscillation circuit 25 is required for having low power consumption so that it can operate for a long time with the small battery BT. Incidentally, there is generally a trade-off relationship between the periodic accuracy of the clock signal and the power consumption and the use of a low-power consumption oscillation circuit reduces the periodic accuracy. When the period accuracy of the first clock signal is ±1%, a measurement corresponding to 24 hours on the basis of the first clock signal may result in a deviation of about 14 minutes from the actual time. If such a time lag with respect to real time occurs, for example, it becomes difficult to perform display or analysis in which the measured heart rate and the activity at that time are linked.

In the embodiment, the time stamp provision unit 22B provides time stamp indicating a measurement time to each measurement result obtained in a cycle longer than the measurement cycle $T_{cycle}$ (here, a cycle for obtaining one measurement result sequence, that is, N measurement results (for example, N is an integer equal to or greater than 2)) among the plurality of measurement results obtained through a plurality of measurements in the measurement cycle $T_{cycle}$ using the measurement unit 22A, particularly, the same type of measurement such as a heart rate on the basis of a second clock signal having a second clock period longer than the first clock period and having better cycle accuracy than the first clock signal. Furthermore, the measurement time correction unit 32B corrects the measurement times of the second to 3600th measurement results other than the first measurement result to which the time stamp is provided in the measurement result sequence in accordance with the measurement period $T_{term}$ of the measurement result sequence specified by the two timestamps provided to each of the Xth and X+1th measurement result sequences and the number of measurement results obtained during the measurement period $T_{term}$. Since the second clock signal has better cycle accuracy than the first clock signal, the time difference between the measurement time corrected on the basis of the time stamp as described above and the real time is small. Furthermore, the power consumption of the first oscillation circuit 25 and the second oscillation circuit 26 is low by deteriorating the cycle accuracy of the first clock signal and lengthening the second clock period to minimize an operation frequency of the second oscillation circuit 26. As described above, according to the embodiment, it is possible to obtain a measurement result to which a measurement time with a small time lag with respect to the real time is provided with low power consumption.

Furthermore, in the embodiment, the time stamp provision unit 22B provides a time stamp to the first measurement result of each of the plurality of measurement result sequences. Furthermore, the measurement time correction unit 32B specifies the measurement period $T_{term}$ in which the N measurement results forming the Xth measurement result sequence are obtained using the difference between the two time stamps provided to the Xth and X+1th measurement result sequences, deletes a measurement result from or adds a new measurement result to a measurement result sequence including N measurement results in accordance with a length of the specified measurement period $T_{term}$, and brings the number of measurement results forming the measurement result sequence closer to the number of measurement results originally obtained in the measurement period $T_{term}$ when the first clock signal does not have a periodic error to correct the measurement time of each measurement result. Although an amount of data required for recording a time stamp increases if the time stamp is added to each measurement result in the measurement result sequence, it is possible to improve the efficiency of recording by providing one time stamp to one measurement result sequence including N measurement results which is a plurality of pieces. When transmitting the recorded measurement results from the sensor device 20 to the management device 30, in addition to being able to record measurement results for a longer time than the recordable capacity, the effect of minimizing the amount of transmission data and minimizing the power consumption related to communication can also be obtained.

The time stamp provision unit 22B does not use the measurement result sequence and may provide a time stamp to these using the first measurement result and the last measurement result among all the measurement results from the start of measurement to the end of measurement in a predetermined measurement period as a measurement result obtained in a cycle longer than the above measurement cycle $T_{cycle}$. However, the measurement time can be corrected with higher accuracy even when the period accuracy of the first clock signal fluctuates due to an influence of heat or the like by dividing all the measurement results in the measurement result sequence and adding a time stamp to each as described above. If the measurement is interrupted by a user's operation or the like during a predetermined measurement period or while obtaining the measurement results constituting the measurement result sequence, the time stamp provision unit 22B may provide the time stamp at that time to the final measurement result. In this case, the measurement time may be corrected on the basis of the period of difference between the time stamp provided to the first measurement result and the time stamp provided to the last measurement result. The time stamp provision unit 22B may provide a time stamp to each of the first measurement result and the last measurement result in one measurement result sequence. The time stamp provision unit 22B may, for example, provide a time stamp to a part of the plurality of measurement results obtained through the plurality of measurements and each of two or more measurement results.

Furthermore, in the embodiment, each of the measurement results includes the results of a first type of measurement which occur irregularly, such as an RRI and the number of steps and the result of a second type of measurement which is continuous such as a heart rate and is different from the first type. Moreover, the measurement time correction unit 32B is configured so that the result of the first type of measurement is not deleted when deleting the measurement result. This prevents discrepancies in measurement results before and after deletion. Particularly, when deleting a measurement result including the result of the first type of measurement, the discrepancy can be effectively prevented by transitioning the result of the first type of measurement to the preceding and succeeding measurement results.

Furthermore, in the embodiment, the measurement time correction unit 32B deletes |M| measurement results from the measurement result sequence when M obtained by the above Expression (2) is negative and adds M new measurement results to the measurement result sequence when M is positive. Thus, the measurement time is corrected with high accuracy.

Furthermore, in the embodiment, the measurement result includes a time interval such as an RRI measured on the basis of the first clock signal and the measurement result correction unit 32C multiplies the time interval measured by the measurement unit 22A by the correction coefficient C calculated by the above Expression (3) to correct the time interval. This also provides accurate time intervals.

MODIFIED EXAMPLES

The present invention is not limited to the above embodiments. Various modifications with respect to the above embodiments are possible. Although modified examples will be listed below, as long as there is no contradiction, the modified examples can be combined at least partially.

Modified Example 1

A hardware configuration of a measurement system 10 is arbitrary. For example, a sensor device 20 may include a pulse wave sensor which is worn on the wrist and detects a pulse waveform, and a measurement unit which measures a pulse from a pulse waveform. The sensor device 20 may include a sensor and a measurement unit for measuring SpO2 (percutaneous arterial oxygen saturation). The sensor device 20 may include other environment sensors capable of measuring humidity or atmospheric pressure, instead of or in addition to the air temperature sensor 27C. Furthermore, the sensor device 20 may include a body motion sensor which measures the number of steps, a posture, or the like from an acceleration, an angular velocity, or the like. The measurement unit 22A may be configured of a device in which each sensor such as an electrocardiographic sensor 27A, an environment sensor, or a body movement sensor and a control unit such as a processor are integrated.

The sensor device 20 may be a measurement device other than a wearable sensor. The object to be measured by the measurement system 10 is not limited to the user's biological information or the like and is arbitrary. It is preferable that the power consumption by measurement be small even if the sensor device 20 is not a wearable sensor or the like and the battery BT is not small. Thus, the trade-off relationship between the periodic accuracy and the power consumption of the clock signal described above can be generally measured. Therefore, even if the sensor device 20 is a measurement device other than a wearable sensor, the measurement system 10 can obtain a measurement result to which a measurement time having a small time deviation with respect to a real time is provided with low power consumption.

The management device 30 may be, for example, a server computer or the like which communicates with the sensor device 20 via a predetermined network other than the smartphone.

The measurement system 10 may be configured as one device in which the units 22A and 22B of the sensor device 20 and the units 32A to 32D of the management device 30 are arranged in one housing. Particularly, the measurement time correction unit 32B and the measurement result correction unit 32C may be configured of the processor 22 of the sensor device 20. Note that the processing load on the sensor device 20 can be reduced by providing the measurement time correction unit 32B and the measurement result correction unit 32C on the management device 30 side as in the above embodiment. At least a part of the units 22A and 22B of the sensor device 20 and the units 32A to 32D of the management device 30 may be realized as a whole by one processor or cooperation of a plurality of processors.

A program which causes the processor to function as at least part of the units 22A and 22B of the sensor device 20 and the units 32A to 32D of the management device 30 is recorded in a computer-readable storage medium. Computer-readable storage media include non-temporary storage media such as hard disks, flash memories, or solid state drives (SSDs).

Modified Example 2

The types of measurement results and the measurement cycle are not limited to those in the above embodiment and measurement results obtained through longer-term measurement may be recorded in the storage device 21 or the storage device 31, for example, by setting the measurement cycle to 1 minute. Furthermore, the electrocardiogram may be measured and the electrocardiogram waveform data may be recorded in the storage device 21 or the storage device 31 by recording the measurement results at 1 ms intervals. The type of measurement and the measurement cycle may be settable by the user.

Modified Example 3

The first oscillation circuit which oscillates the first clock signal may be a clock oscillation circuit included in an analog-to-digital (A/D) conversion integrated circuit (IC) for measurement included in the electrocardiographic sensor 27A or the like. In this case, the measurement unit 22A may include an electrocardiographic sensor 27A and the like and measure the electrocardiographic potential and the like using the clock signal of the A/D conversion IC as a first clock signal. In addition, the time stamp provision unit 22B may provide a time stamp to a measurement result such as an electrocardiographic potential obtained through measurement. The second oscillation circuit may be a real time clock IC provided separately from the processor 22. In this case, the time stamp provision unit 22B may be configured to include the real time clock IC.

Modified Example 4

The time stamp provision unit 22B may provide time stamp to the measurement results obtained at regular intervals (for example, every hour), instead of the number of measurement results. Also, the measurement time correction unit 32B may be configured to correct the measurement time by specifying the number of measurement results obtained in a certain period of time and deleting the measurement result from or adding a new measurement result to the measurement result sequence including the measurement results obtained in the fixed period in accordance with the specified number. For example, when the number of specified measurement results is N, the measurement cycle based on the first clock signal when there is no periodic error is $T_{cycle}$ and the certain period is $T_{term}$ (fixed value), the measurement time correction unit 32B adds or deletes M measurement results in accordance with the sign of M obtained through the above Expression (2).

It can be said that, when M is positive, the measurement time correction unit 32B reduces the number N of the specified measurement results by M from the original number of measurement results obtained in the fixed period when the first clock signal does not have a periodic error. In this case, the measurement time correction unit 32B adds M measurement results. It can be said that, when M is negative, the measurement time correction unit 32B makes the number N of specified measurement results |M| greater than the number of the original measurement results. In this case, the measurement time correction unit 32B deletes |M| pieces of measurement results. In this way, the measurement time correction unit 32B may delete or add measurement results so that the number of measurement results obtained in a fixed period which is an interval in which two time stamps is provided is brought closer to the number of measurement results originally obtained in the fixed period when the first clock signal does not have a periodic error.

Modified Example 5

For example, as shown in FIG. 12, the measurement time correction unit 32B may associate each measurement result in the corrected measurement result sequence with the measurement time of each measurement result and record them in the storage device 31. The measurement time of each measurement result is calculated through, for example, the above Expression (1).

Modified Example 6

The measurement time correction unit 32B may calculate a numerical value obtained by dividing the period in which the measurement results constituting the measurement result sequence specified by the time stamp were obtained by the number of measurement results obtained in the period and calculate the actual measurement cycle in the period. The measurement time correction unit 32B may correct the measurement time of each measurement result in the measurement result sequence on the basis of the measurement cycle without deleting or adding the measurement result from or to the measurement result sequence. For example, the measurement time Tm of each measurement result may be calculated through the above Expression (1) in which $T_{cycle}$ is the calculated measurement cycle. The measurement time correction unit 32B may associate each instrumentation result in the measurement result sequence with the measurement time of each measurement result calculated above and record them in the storage device 31, as in Modified Example 5.

REFERENCE SIGNS LIST

10 Measurement system
20 Sensor device
21 Storage device
22 Processor
22A Measurement unit
22B Time stamp provision unit
23 RAM
25 First oscillation circuit
26 Second oscillation circuit
27A Electrocardiographic sensor
27B Acceleration sensor
27C Air temperature sensor
30 Management device
31 Storage device
32 Processor
32A Measurement result recording unit
32B Measurement time correction unit
32C Measurement result correction unit
32D Measurement result usage unit
33 RAM
35 Input/output device

The invention claimed is:

1. A measurement system, comprising:
one or more processors;
one or more storage devices storing one or more programs for execution by the one or more processors;
a first oscillator configured to oscillate a first clock signal having a first clock period;
a second oscillator configured to oscillate a second clock signal having a second clock period longer than the first clock period and with higher period accuracy than the first clock period;
a measurement device executing on at least one of the one or more processors and configured to perform measurement a plurality of times to obtain a plurality of measurement results, the measurement device configured to operate on a first basis of the first clock signal having the first clock period;
a time stamp provision circuit executing on at least one of the one or more processors and configured to provide a time stamp indicating a measurement time to each of two or more of the plurality of measurement results obtained through the measurement device, the time stamp provision circuit configured to provide the time stamp to each of two or more of the plurality of measurement results on a second basis of the second clock signal having the second clock period; and
a measurement time correction circuit executing on at least one of the one or more processors and configured to correct a measurement time of a measurement result other than the measurement result to which the time stamp is provided to obtain a corrected measurement result, the corrected measurement result being among the measurement results obtained during a period specified using two time stamps of the time stamps provided to each of the two or more of the plurality of measurement results.

2. The measurement system according to claim 1, wherein:
the plurality of measurement results obtained using the measurement device includes a plurality of measurement result sequences, one measurement result sequence being N measurement results obtained through consecutive N measurements,
the time stamp provision circuit is further configured to add the time stamp to a first measurement result of each of the plurality of measurement result sequences, and
the measurement time correction circuit is further configured to:
specify a measurement period in which the N measurement results of the measurement result sequence are obtained using a difference between the two time stamps;
delete a measurement result from or add a new measurement result to a measurement result sequence in accordance with a length of the specified measurement period; and
bring a first number of measurement results of the measurement result sequence closer to a second number of measurement results obtained in the measurement period when the first clock signal does not have a periodic error to correct the measurement time.

3. The measurement system according to claim 2, wherein each of the plurality of measurement results includes a first type of measurement result and a second type of measurement result different from the first type, and the measurement time correction circuit is configured so that the result of the first type of measurement is not deleted when deleting the measurement result.

4. The measurement system according to claim 2, wherein the measurement time correction circuit is configured to, when a period of the measurement based on the first clock signal when there is no periodic error is $T_{cycle}$ and the measurement period is $T_{term}$, delete |M| measurement results from the measurement result sequence when M obtained by the following Expression (A) is negative and add M new measurement results to the measurement result sequence when the M is positive:

$$M=\text{int}(T_{term}/T_{cycle})-N \tag{A}$$

where, $\text{int}(T_{term}/T_{cycle})$ is an integer conversion operation of a value obtained through $T_{term}/T_{cycle}$.

5. The measurement system according to claim 2, wherein the measurement result includes a time interval measured on the first basis of the first clock signal, and
the measurement system further includes a measurement result correction circuit executing on at least one of the one or more processors and configured to correct the time interval by multiplying the time interval by a correction coefficient C calculated by the following Expression (B):

$$C=T_{term}/(T_{cycle}\times N) \tag{B}$$

when $T_{cycle}$ is a cycle of the measurement based on the first clock signal when there is no periodic error, and $T_{term}$ is the measurement period in the measurement system.

6. A measurement method, comprising:
performing measurement a plurality of times on a first basis of a first clock signal having a first clock period to obtain a plurality of measurement results, wherein the first clock signal having the first clock period is oscillated by a first oscillator;

providing a time stamp indicating a measurement time to each of two or more of the plurality of measurement results obtained through performing the measurement on a second basis of a second clock signal having a second clock period, wherein:

the second clock signal having the second clock period is oscillated by a second oscillator, and the second clock period is longer than the first clock period and has higher accuracy than the first clock period; and correcting a measurement time of a measurement result other than the measurement result to which the time stamp is provided among the measurement results obtained during a period specified using two time stamps of the time stamps provided to each of the two or more of the plurality of measurement results.

7. The measurement method of claim 6, wherein:

the plurality of measurement results are obtained using a measurement device, the plurality of measurement results obtained using the measurement device includes a plurality of measurement result sequences, one measurement result sequence being N measurement results obtained through consecutive N measurements, and the measurement method further comprises:

adding the time stamp to a first measurement result of each of the plurality of measurement result sequences, specifying a measurement period in which the N measurement results of the measurement result sequence are obtained using a difference between the two time stamps, deleting a measurement result from or add a new measurement result to a measurement result sequence in accordance with a length of the specified measurement period, and bringing a first number of measurement results of the measurement result sequence closer to a second number of measurement results obtained in the measurement period when the first clock signal does not have a periodic error to correct the measurement time.

8. The measurement method of claim 7, wherein each of the plurality of measurement results includes a first type of measurement result and a second type of measurement result different from the first type, and wherein the result of the first type of measurement is not deleted when deleting the measurement result.

9. The measurement method of claim 7, further comprising:

when a period of the measurement based on the first clock signal when there is no periodic error is $T_{cycle}$ and the measurement period is $T_{term}$, deleting $|M|$ measurement results from the measurement result sequence when M obtained by the following Expression (A) is negative and adding M new measurement results to the measurement result sequence when the M is positive:

$$M=\text{int}(T_{term}/T_{cycle})-N \qquad (A)$$

where, int $(T_{term}/T_{cycle})$ is an integer conversion operation of a value obtained through $T_{term}/T_{cycle}$.

10. The measurement method of claim 7, wherein the measurement result includes a time interval measured on the first basis of the first clock signal, and the method further comprises:

correcting the time interval by multiplying the time interval by a correction coefficient C calculated by the following Expression (B):

$$C=T_{term}/(T_{cycle}\times N) \qquad (B)$$

when $T_{cycle}$ is a cycle of the measurement based on the first clock signal when there is no periodic error, and $T_{term}$ is the measurement period in a measurement system.

11. A non-transitory computer readable storage medium storing a program causing a computer which acquires a plurality of measurement results obtained by performing measurement a plurality of times on a first basis of a first clock signal having a first clock period and a time stamp indicating a measurement time provided to each of two or more of the plurality of measurement results on a second basis of a second clock signal having a second clock period, to function as:

a measurement time correction circuit configured to correct a measurement time of a measurement result other than the measurement result to which the time stamp is provided among the measurement results obtained during a period specified using two time stamps of the time stamps provided to each of the two or more of the plurality of measurement results, in accordance with the period and a number of measurement results obtained during the period among the plurality of measurement results, wherein:

the first clock signal having the first clock period is oscillated by a first oscillator, the second clock signal having the second clock period is oscillated by a second oscillator, the second clock period is longer than the first clock period, and the second clock period has higher accuracy than the first clock period.

* * * * *